United States Patent
Dewis et al.

(10) Patent No.: US 7,427,421 B2
(45) Date of Patent: *Sep. 23, 2008

(54) SATURATED AND UNSATURATED N-ALKAMIDES EXHIBITING TASTE AND FLAVOR ENHANCEMENT EFFECT IN FLAVOR COMPOSITIONS

(75) Inventors: Mark L. Dewis, Matawan, NJ (US); Garry Conklin, Pequannock, NJ (US); Tao Pei, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 508 days.

This patent is subject to a terminal disclaimer.

(21) Appl. No.: 10/939,096

(22) Filed: Sep. 10, 2004

(65) Prior Publication Data

US 2006/0057268 A1 Mar. 16, 2006

(51) Int. Cl.
A23L 1/22 (2006.01)

(52) U.S. Cl. .......... 426/534; 426/650; 554/35; 554/69

(58) Field of Classification Search ........ 426/534, 426/536, 537, 538, 650; 554/35, 69
See application file for complete search history.

(56) References Cited

U.S. PATENT DOCUMENTS

| | | |
|---|---|---|
| 3,111,127 A | 11/1963 | Jarboe |
| 4,029,759 A | 6/1977 | Humbert et al. |
| 4,032,661 A | 6/1977 | Rowsell et al. |
| 4,150,052 A | 4/1979 | Watson et al. |
| 4,153,679 A | 5/1979 | Rowsell et al. |

(Continued)

FOREIGN PATENT DOCUMENTS

EP 1 121 927 A2 2/2001

(Continued)

OTHER PUBLICATIONS

English abstract of Saureamide In Hochruckextrakten Aus Muntokpfeffer in English. H. Kollmannsberger und S. Nitz, Chem. Mikrobiol. Technol. Lebensm. 14, 87-94 (1992).
"Pellitorine Isomers. II. The Synthesis of N-Isobutyl-trans-2, trans-4-decadienamide[1,2,3]", Martine Jacobson, vol. 75, Jun. 5, 1953, pp. 2584-2586.
"Alkamides from Artemisia dracunculus", Bouchra Saadali et al., Phytochemistry, Pergamon Press, vol. 58, No. 7, Dec. 2001, pp. 1083-1086.
"Isobutylamide numbing agents of toothache grass, Ctenium aromaticum" Rubi Gamboa-Leon et al., Biochemical Systematics and ecology, vol. 28, 2000, pp. 1019-1021.
Search for Unsaturated Dienoic Acid Compounds GRAS Flavoring Substances 20, Food Technology, vol. 55, No. 12, Dec. 2001 at p. 53.
Rule, et al, Optical Activity and the Polarity of Substituent Groups Part VIII. Growing-chain Effects and the Ortho-Effect in Benzoic Esters, J. Chem. Soc. 1928 (Part I), pp. 1347-1361.
SciFinder (Nov. 20, 2002; Trademark of Chemical Abstracts Service), to wit: malonamic acid, p-menth-3-yl ester, ±—(8C1) having CAS Registry No. 6129-88-0.

(Continued)

Primary Examiner—Carol Chaney
Assistant Examiner—Nikki H Dees
(74) Attorney, Agent, or Firm—Elizabeth M. Quirk; XuFan Tseng; Joseph F. Leightner

(57) ABSTRACT

Saturated and unsaturated compounds having sweet, salt or umami taste enhancement qualities. The compounds have the structure:

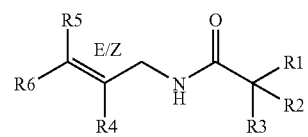

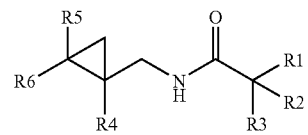

where $R^1$=H or methyl;
$R^2$ is selected from the group consisting of H, C1-C4 alkyl, alkenyl and methylene;
$R^3$ is selected from the group consisting of H, C1-C8 straight or branched chain alkyl, alkenyl, dienalkyl or phenyl;
or if $R^1$=H, $R^2$ and $R^3$ taken together can represent

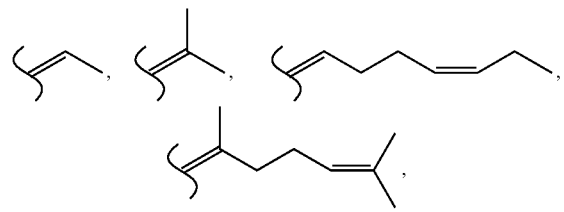

cyclopropyl, cyclobutyl, cyclopentyl, cyclopentenyl, cyclohexyl, or cyclohexenyl;
$R^4$ is selected from the group consisting of H, methyl and ethyl;
$R^5$ is selected from the group consisting of H, methyl and ethyl;
$R^6$ is selected from the group consisting of H, C1-C9 straight or branched chain alkyl, alkenyl, alkyldienyl, acyclic or containing no more than one ring;
with the proviso that in structure 1 when $R^4$ is H or Me; and $R^5$=H or methyl, $R^6$ may be selected from the group described above or phenyl.

25 Claims, No Drawings

U.S. PATENT DOCUMENTS

| | | | |
|---|---|---|---|
| 4,185,106 A | 1/1980 | Dittmar et al. |
| 4,226,988 A | 10/1980 | Watson et al. |
| 4,296,093 A | 10/1981 | Rowsell et al. |
| 4,470,982 A | 9/1984 | Winkler |
| 4,472,421 A | 9/1984 | Buchel et al. |
| 5,009,893 A | 4/1991 | Cherukuri et al. |
| 5,545,424 A | 8/1996 | Nakatsu et al. |
| 5,624,666 A | 4/1997 | Coffindaffer et al. |
| 5,641,480 A | 6/1997 | Vermeer |
| 5,725,865 A | 3/1998 | Mane et al. |
| 5,730,965 A | 3/1998 | Rapaport |
| 5,843,466 A | 12/1998 | Mane et al. |
| 5,955,066 A | 9/1999 | Sako et al. |
| 6,110,520 A | 8/2000 | He et al. |
| 6,200,554 B1 | 3/2001 | Yeoh et al. |
| 6,210,695 B1 | 4/2001 | Beerse et al. |
| 6,248,315 B1 | 6/2001 | Young et al. |
| 6,251,463 B1 | 6/2001 | Rossy et al. |
| 6,294,186 B1 | 9/2001 | Beerse et al. |
| 6,297,203 B1 | 10/2001 | Guskey et al. |
| 6,299,900 B1 | 10/2001 | Reed et al. |
| 6,303,817 B1 | 10/2001 | Boden et al. |
| 6,328,982 B1 | 12/2001 | Shiroyama et al. |
| 6,333,180 B1 | 12/2001 | Farbood et al. |
| 6,338,855 B1 | 1/2002 | Albacarys et al. |
| 6,365,215 B1 | 4/2002 | Grainger et al. |
| 6,365,601 B1 | 4/2002 | Gaikar et al. |
| 6,391,886 B1 | 5/2002 | Lee |
| 6,451,844 B1 | 9/2002 | Watkins et al. |
| 6,455,080 B1 | 9/2002 | Wolf et al. |
| 6,572,914 B1 | 6/2003 | Borlinghaus |
| 6,579,513 B1 | 6/2003 | Tashjian et al. |
| 6,579,514 B1 | 6/2003 | Hall et al. |
| 6,579,516 B1 | 6/2003 | Mansouri |
| 6,579,535 B2 | 6/2003 | Valentine et al. |
| 6,579,543 B1 | 6/2003 | McClung |
| 2001/0032645 A1 | 10/2001 | Cronk et al. |
| 2002/0012640 A1 | 1/2002 | Mohammadi et al. |
| 2002/0142015 A1 | 10/2002 | Kumamoto et al. |
| 2002/0173436 A1 | 11/2002 | Sonnenberg et al. |
| 2003/0072842 A1 | 4/2003 | Johnson et al. |
| 2003/0082124 A1 | 5/2003 | Hammer |
| 2003/0082129 A1 | 5/2003 | Buckingham et al. |
| 2003/0082271 A1 | 5/2003 | Wolf et al. |
| 2003/0095936 A1 | 5/2003 | Light |
| 2003/0113357 A1 | 6/2003 | Bell et al. |
| 2003/0152682 A1 | 8/2003 | Ley et al. |
| 2004/0241312 A1 | 12/2004 | Gatfield et al. |
| 2005/0084506 A1* | 4/2005 | Tachdjian et al. .......... 424/400 |

FOREIGN PATENT DOCUMENTS

| | | |
|---|---|---|
| EP | 1 121 927 A2 | 8/2001 |
| EP | 1 122 233 A1 | 8/2001 |
| GB | 1 438 205 | 3/1976 |
| JP | 04 803546 | 12/1970 |
| JP | 56087505 | 7/1981 |
| WO | WO 93/23005 | 11/1993 |
| WO | WO 98/07404 | 2/1998 |
| WO | WO 99/07235 | 2/1999 |
| WO | WO 00/45815 | 8/2000 |
| WO | WO 02/051392 | 4/2002 |
| WO | WO 2004/000787 A2 | 12/2003 |
| WO | WO2004/011415 | 2/2004 |
| WO | WO 2004/043906 | 5/2004 |

OTHER PUBLICATIONS

Jaloner, et al, A Molecular Approach to Flavor Synthesis. I. Menthol Esters of Varying Size and Polarity, Journal of Polymer Science:Polymer Chemistry Edition, vol. 18, 2933-2940 (1980).

Ottinger, et al, Systematic Studies on Structure and Physiological Activity of Cyclic Alpha-Keto Enamines, a Novel Class of "Cooling" Compounds, J.Agric.Food Chem., 2001, 49, 5383-5390.

ACS Symposium Series 867, Challenges in Taste Chemistry and Biology, Sponsored by the ACS Division of Agricultural and Food Chemistry, Chapter 9, Pungent and Tingling Compounds in Asian Cuisine, Galopin, et al, pp. 139-152.

Prior Art Submission Under 37 CFR 1.291.

U.S. Appl. No. 10/411,672, filed Apr. 11, 2003, Dewis, et al.

U.S. Appl. No. 10/643,542, filed Aug. 19, 2003, Flammer, et al.

"Pungent Alkamides from Spilantes Acmella L. Var. Oleracea Clarke," Nakatani N et al. Bioscience Biotechnology Biochemistry, Japan Soc. For Bioscience Biotechnology and Agrochem., vol. 56, No. 5, 1992, pp. 759-762.

Databse Beilstein, Beilstein Institute for Organic Chemistry, J. Chem. Soc., 1952, p. 4338.

"Amides of vegetable origin. VII. Synthesis of N-isobutyldodeca-trans-2, trans-4, trans-8-ans trans-2, trans-4, cis-8-trienamide and the relation to Sanshool I," Crombie L. et al., Journal of Chemical Society, Abstracts, pp. 4244-4249, 1955.

"Isobutylamide numbing agents of toothache grass, Ctenium aromaticum," Rubi Gamboa-Leon et al., Biochemical Systematics and Ecology, 28(10), 2000, pp. 1019-1021..

"Structure and synthesis of a new hypotensive vasodilator isolated from Spreptomyces aerofaciens," Tanaka, Hirokazu et al., Tetrahedron Letters 22(35), 1981, pp. 3421-3422.

* cited by examiner

SATURATED AND UNSATURATED N-ALKAMIDES EXHIBITING TASTE AND FLAVOR ENHANCEMENT EFFECT IN FLAVOR COMPOSITIONS

FIELD OF THE INVENTION

Saturated and unsaturated N-alkamide compounds having sweet, salt or umami taste and flavor enhancement quality.

BACKGROUND OF THE INVENTION

The term Umami, from the Japanese word to describe savory or meaty, is the term used to describe the unique overall fullness, savory or salivatory taste of food. Materials that exhibit this taste quality generally potentate the intensity of glutamate solutions and this is one important characteristic of umami taste. It is increasingly becoming recognized as the fifth sense of taste, the others being sour, sweet, salt and bitter. Compounds traditionally described as possessing this character are monosodium glutamate (MSG), protein hydrolysates, some amino acids and certain nucleotides and phosphates.

MSG is the most widely used material as a 'taste enhancer' where it synergizes the perception of 'savory' ingredients, but has also been alleged to cause allergic reaction to a proportion of the population.

Among other chemical compounds, several nucleotides have also been described to exhibit the umami effect including Adenosine 5'-(trihydrogen diphosphate), 5'-Cytidylic acid (5'-CMP), 5'-Uridylic acid (5'-UMP), 5'-Adenylic acid (5'-AMP), 5'-Guanylic acid (5'-GMP), 5'-Inosinic acid (5'-IMP) and the di-sodium salts of 5'-Guanylic acid and 5'-Inosinic acid.

Recent literature cites an extensive range of other organic compounds as taste active components of mixtures shown to give the umami taste effect. These include but are not necessarily limited to: organic acids such as succinic acid, lactic acid, saturated straight chain aliphatic acids of six, eight, fourteen, fifteen, sixteen, and seventeen carbon chain lengths, Z4,Z7,Z10,Z13,Z16,Z19-docosahexaenoic acid, Z5,Z8,Z11, Z14,Z17-eicosapentaenoic acid, Z9,Z12,Z16,Z19-octadecadienoic acid, Z9-octadecenoic acid, glutaric acid, adipic acid, suberic acid, and malonic acid. Amino acids having umami effects reported in the literature include glutamic acid, aspartic acid, threonine, alanine, valine, histidine, praline, tyrosine, cystine, methionine, pyroglutamic acid, leucine, lycine, and glycine. Dipeptides possessing umami properties include Val-Glu and Glu-Asp.

Other miscellaneous compounds having umami properties include alpha-amino adipic acid, malic acid, alpha-aminobutyric acid, alpha-aminoisobutyric acid, E2,E4-hexadienal, E2,E4-heptadienal, E2,E4-octadienal, E2,E4-decadienal, Z4-heptenal, E2,Z6-nonadienal, methional, E3,E5-octadien-2-one, 1,6-hexanediamine, tetramethylpyrazine, trimethylpyrazine, cis-6-dodecen-4-olide, glutamate glycoconjugates, fish sauce blended with anchovy paste (U.S. Patent Application 2003/0142090) and a number of naturally occurring amino-acids.

Additionally, a variety of molecules are known by those skilled in the art to provide salt enhancement, these include but are not limited to Adenosine 5'-(trihydrogen diphosphate), 5'-Cytidylic acid (5'-CMP), 5'-Uridylic acid (5'-UMP), 5'-Adenylic acid (5'-AMP), 5'-Guanylic acid (5'-GMP), 5'-Inosinic acid (5'-IMP) and the di-sodium salts of 5'-Guanylic acid and 5'-Inosinic acid, (+)-(S)-Alapyridaine (chemical name N-(1-Carboxyethyl)-6-hydroxymethyl pyridinium-3-ol), succinic acid, cetylpyridinium chloride, bretylium tosylate, various polypeptides, mixtures of calcium salts of ascorbic acid, potassium chloride, calcium chloride, magnesium chloride, arginine ammonium chloride, alpha-amino acids and their corresponding hydrogen chloride, ammonium and sodium salts and a number of natural plant extracts. Uses of these materials are described in various U.S. Pat. Nos. 4,997,672; 5,288,510; 6,541,050, U.S. Patent Application 2003/0091721 and Eur. Pat. Appl. 2003/1291342.

Addtionally, choline chloride has been shown to enhance salt and increase palatability of sodium chloride reduced systems, Physiol Behav. 1994, 55(6), 1039-46.

In addition to this work, our work has included the identification of new flavor materials described in U.S. Ser. No. 10/919,631 filed on Aug. 17, 2004; U.S. Ser. No. 10/861,751 filed on Jun. 4, 2004; and U.S. Ser. No. 10/783,652 filed Feb. 20, 2004.

Despite these disclosures there is an ongoing need for new flavor ingredients particularly those that exhibit advantageous properties for flavor enhancement or modulation, or more preferably the lowering of MSG and/or salt levels in foodstuffs.

SUMMARY OF THE INVENTION

The present invention relates to novel compounds and a process for augmenting or imparting a flavor enhancement effect or modifying the perception of one or more of the five basic taste qualities sweet, sour, salt, bitter and umami, to a foodstuff, chewing gum, medicinal product, toothpaste, alcoholic beverage, aqueous beverage, snack, sauce or soup comprising the step of adding to a foodstuff, chewing gum, medicinal product, toothpaste, alcoholic beverage, aqueous beverage, snack, sauce or soup a flavor enhancement or modification of basic taste quality augmenting, enhancing or imparting quantity and concentration of at least one N-substituted unsaturated alkyl amide defined according to the structures:

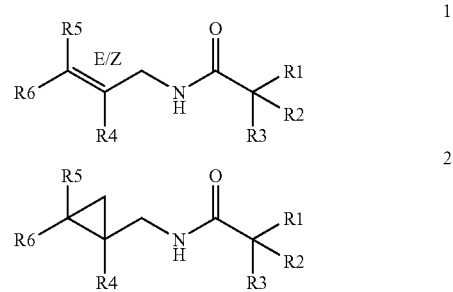

where $R^1$=H or methyl;

$R^2$ is selected from the group consisting of H, C1-C4 alkyl, alkenyl and methylene;

$R^3$ is selected from the group consisting of H, C1-C8 straight or branched chain alkyl, alkenyl, dienalkyl and phenyl;

or if $R^1$=H, $R^2$ and $R^3$ taken together can represent

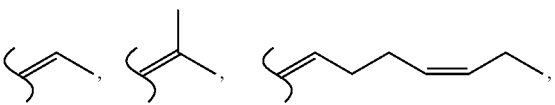

-continued

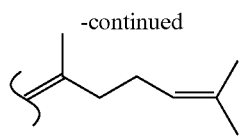

cyclopropyl, cyclobutyl, cyclopentyl, cyclopentenyl, cyclohexyl, or cyclohexenyl;
$R^4$ is selected from the group consisting of H, methyl or ethyl;
$R^5$ is selected from the group consisting of H, methyl and ethyl;
$R^6$ is selected from the group consisting of H, C1-C9 straight or branched chain alkyl, alkenyl, alkyldienyl, acyclic or containing no more than one ring;
except for in the case of structure 1 when if $R^4$=H or methyl and $R^5$=H or methyl, $R^6$ as described above and phenyl.

The above formulae define novel compounds with the proviso that in structure 1, if $R^1$=H and $R^2$=H, then $R^3$ can not be H or methyl.

As used herein compounds described in structure 2 will be referred to as "cyclopropylic amides".

In addition to the novel compounds and the use of the compounds to enhance the taste of foodstuffs by the incorporation of the above ingredients and others set forth in this specification in foodstuff and other materials.

DETAILED DESCRIPTION OF THE INVENTION

The formula set forth above describes a general class of novel materials that we have found to enhance the flavor characteristics of food.

In a more preferred embodiment of the invention the amides have the structure set forth in 1 and 2 with wherein
$R^1$=H or methyl;
$R^2$ is selected from the group consisting of H, methyl, and ethyl;
$R^3$ is selected from the group consisting of H, C1-C4 alkyl, or alkenyl, or if $R^1$=H, $R^2$ and $R^3$ taken together can represent

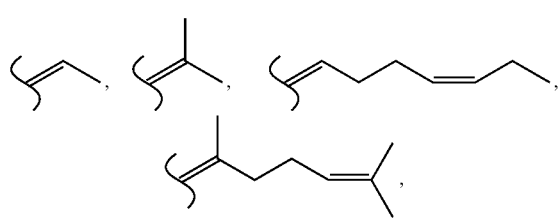

cyclopropyl, cyclopentyl, cyclopentenyl, cyclohexyl or cyclohexenyl;
$R^4$ is selected from the group consisting of H or methyl;
$R^5$ is selected from the group consisting of H or methyl; and
$R^6$ is selected from the group consisting of C3-C7 straight or branched chain alkyl, or alkenyl, acyclic or containing no more than one ring, and in the case of structure 1, phenyl.

The above compounds of the present invention can be used in accordance with the present method in enhancing the salt and umami effects in foods. The above compounds are also novel with the proviso that in structure 1, if $R^1$=H and $R^2$=H, then $R^3$ can not be H or methyl.

In a highly preferred embodiment of the invention the amides have the structure set forth below:

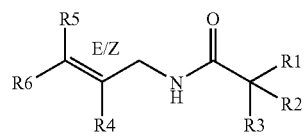

Formula I wherein:
$R^1$=H or methyl;
$R^2$ is selected from the group consisting of H and methyl;
$R^3$ is selected from the group consisting of H, methyl, ethyl, allyl, isopropyl and propyl;
or if $R^1$ is H, $R^2$ and $R^3$ taken together is selected from the group consisting of

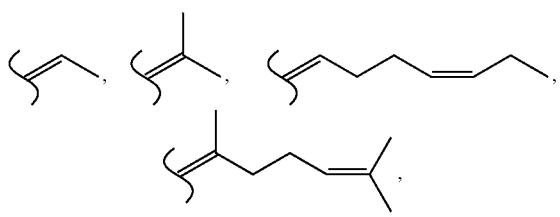

cyclopropyl, cyclopentyl, cyclopentenyl, cyclohexyl and cyclohexenyl;
$R^4$ is selected from the group consisting of H or methyl;
$R^5$ is selected from the group consisting of H or methyl; and
$R^6$ is selected from the group consisting of six carbon straight or branched chain alkyl, alkenyl, cyclohexenyl and phenyl.

The above compounds of the present invention can be used in accordance with the present method in enhancing the salt and umami effects in foods. The above compounds are also novel with the proviso that in Formula I, if $R^1$=H and $R^2$=H, then $R^3$ can not be H or methyl.

As used herein the compounds under structure 1 and formula 1 will be referred to as "alkenylamides".

In the most preferred embodiment of the invention the amides have the structure set forth below:

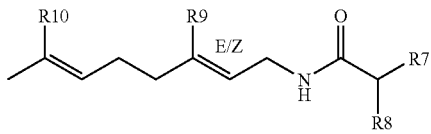

Formula II wherein: $R^7$ is selected from the group consisting of H or methyl, $R^8$ is selected from the group consisting of H or methyl, or $R^7$ and $R^8$ taken together can represent cyclopropyl,

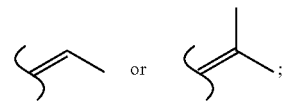

$R^9$ is selected from the group consisting of H or methyl; and $R^{10}$ is selected from the group consisting of H or methyl.

The above compounds of the present invention can be used in accordance with the present method in enhancing the salt and umami effects in foods. The above compounds are also novel with the proviso that in Formula II, if $R^7$=H, then $R^8$ can not be H or methyl.

As used herein the most preferred compounds will be referred to hereinafter as dienalkylamides.

As used throughout the application,

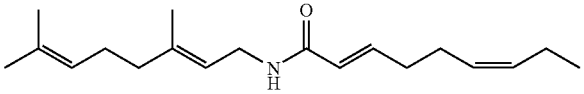

is understood to represent an alkene terminus as depicted in $R^2$, $R^3$, $R^7$ and $R^8$ with an attachment to the alpha carbon of the acid moiety in structures 1 and 2 and Formule 1 and 2 set forth in the examples.

In the following tables and as used in the specification, Me is understood to be a methyl group and Et is understood to be an ethyl group.

Our invention specifically relates to the novel compositions according to the formula I above:

| $R^1$ | $R^2$ | $R^3$ | $R^4$ | $R^5$ | $R^6$ | Compound Double bond configuration as per drawing |
|---|---|---|---|---|---|---|
| H | 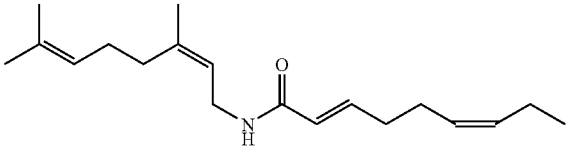 | | H | Me | $(CH_3)_2C=CHCH_2CH_2$ | |
| H | 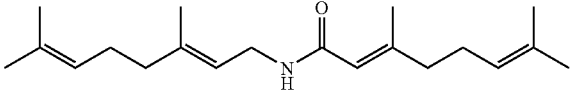 | | H | Me | $(CH_3)_2C=CHCH_2CH_2$ | |
| H | 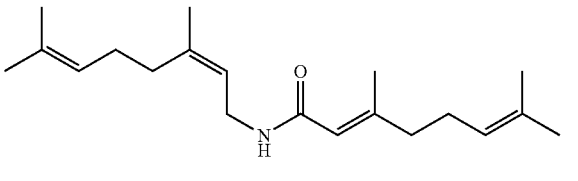 | | H | Me | $(CH_3)_2C=CHCH_2CH_2$ | |
| H | | | H | Me | $(CH_3)_2C=CHCH_2CH_2$ | |
| H | 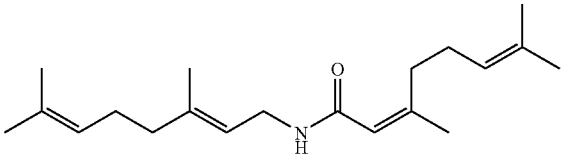 | | H | Me | $(CH_3)_2C=CHCH_2CH_2$ | |
| H | 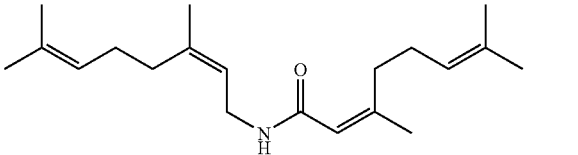 | | H | Me | $(CH_3)_2C=CHCH_2CH_2$ | |
| H | 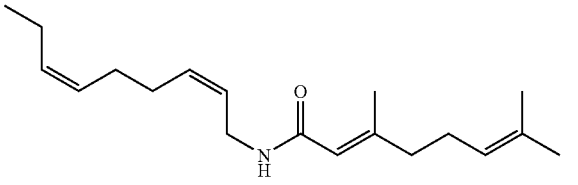 | | H | H | $CH_3CH_2CH=CHCH_2CH_2$ | |

-continued
| R¹ | R² | R³ | R⁴ | R⁵ | R⁶ | Compound Double bond configuration as per drawing |
|---|---|---|---|---|---|---|
| H | 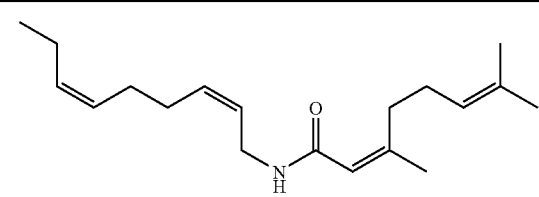 | | H | H | CH₃CH₂CH=CHCH₂CH₂ | 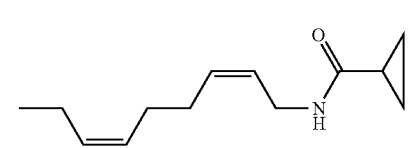 |
| H | cyclopropyl | | H | H | CH₃CH₂CH=CHCH₂CH₂ | 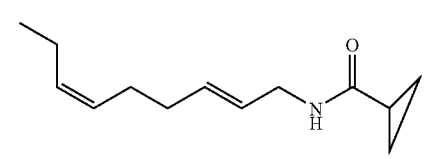 |
| H | cyclopropyl | | H | H | CH₃CH₂CH=CHCH₂CH₂ | 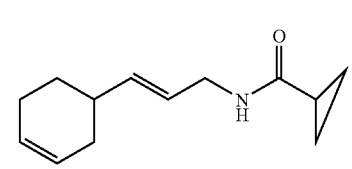 |
| H | cyclopropyl | | H | H | 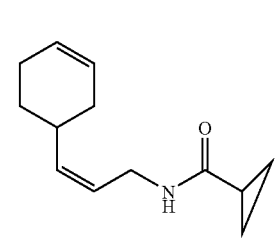 | 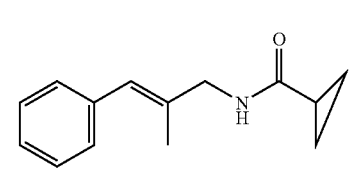 |
| H | cyclopropyl | | H | H | 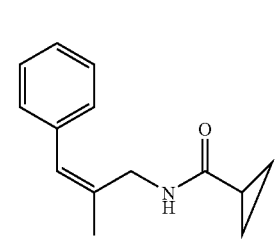 | 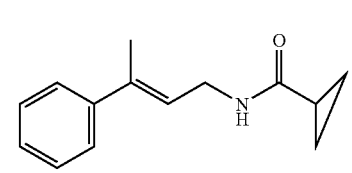 |
| H | cyclopropyl | | Me | H |  |  |
| H | cyclopropyl | | Me | H |  |  |
| H | cyclopropyl | | H | Me |  |  |

-continued
| R¹ | R² | R³ | R⁴ | R⁵ | R⁶ | Compound Double bond configuration as per drawing |
|---|---|---|---|---|---|---|
| H | cyclopropyl | | H | Me |  | 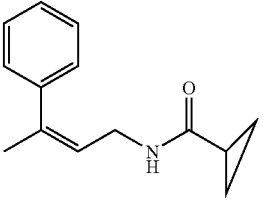 |
| H | cyclopropyl | | Me | H | CH₃CH₂CH=CHCH₂ | 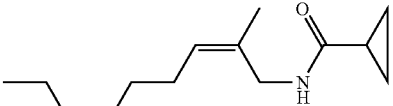 |
| H | cyclopropyl | | Me | H | CH₃CH₂CH=CHCH₂ | 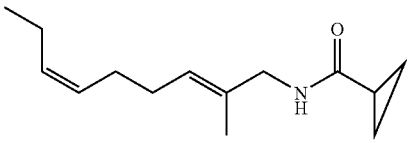 |
| H | cyclopropyl | | H | H |  | 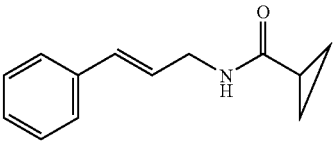 |
| H | cyclopropyl | | H | H |  | 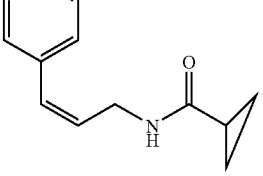 |
| Me | Me | Me | H | Me | (CH₃)₂C=CHCH₂CH₂ | 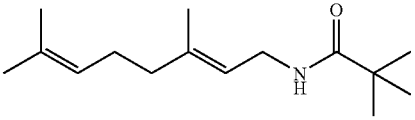 |
| Me | Me | Me | H | Me | (CH₃)₂C=CHCH₂CH₂ | 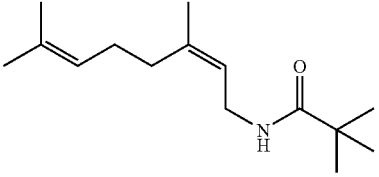 |
| H | H | Et | H | Me | (CH₃)₂C=CHCH₂CH₂ | 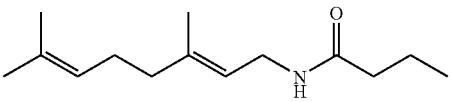 |
| H | H | Et | H | Me | (CH₃)₂C=CHCH₂CH₂ | 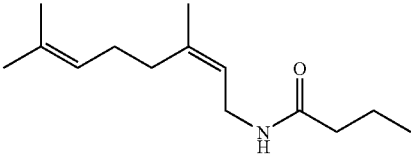 |

-continued

| R¹ | R² | R³ | R⁴ | R⁵ | R⁶ | Compound Double bond configuration as per drawing |
|----|----|----|----|----|----|----------------------------------------------------|
| Me | H | H | Me | H | phenyl | structure |
| Me | H | H | Me | H | phenyl | structure |
| Me | H | H | H | Me | phenyl | structure |
| Me | H | H | H | Me | phenyl | structure |
| H | H | H | Me | H | phenyl | structure |
| H | H | H | Me | H | phenyl | structure |
| H | H | H | H | Me | phenyl | structure |
| H | H | H | H | Me | phenyl | structure |

-continued

| R¹ | R² | R³ | R⁴ | R⁵ | R⁶ | Compound Double bond configuration as per drawing |
|---|---|---|---|---|---|---|
| H | H | H | Me | H | CH₃CH₂CH=CHCH₂CH₂ | |
| H | H | H | Me | H | CH₃CH₂CH=CHCH₂CH₂ | |
| H | H | Me | H | H | (cyclohexenyl)CH | |
| H | H | Me | H | H | (cyclohexenyl)CH | |
| H | H | H | H | H | (cyclohexenyl)CH | |
| H | H | H | H | H | (cyclohexenyl)CH | |
| Me | Me | Me | H | H | (cyclohexenyl)CH | |
| Me | Me | Me | H | H | (cyclohexenyl)CH | |
| Me | H | Et | H | Me | (CH₃)₂C=CHCH₂CH₂ | |

-continued

| R¹ | R² | R³ | R⁴ | R⁵ | R⁶ | Compound Double bond configuration as per drawing |
|---|---|---|---|---|---|---|
| Me | H | Et | H | Me | (CH₃)₂C=CHCH₂CH₂ | |

Refering to Formula II above, the present invention relates to the novel compositions according to the formula II above:

| R⁷ | R⁸ | R⁹ | R¹⁰ | Geranyl 2,3-double Bond configuration | Compound |
|---|---|---|---|---|---|
| Cyclopropyl | Me | Me | | E | |
| Cyclopropyl | Me | Me | | Z | |
| Me | Me | Me | Me | E | |
| Me | Me | Me | Me | Z | |
| ⌇CH=CHCH₃ | | Me | Me | E | |
| ⌇CH=CHCH₃ | | Me | Me | Z | |
| ⌇C=C(CH₃)₂ | | Me | Me | E | |

-continued

| $R^7$ | $R^8$ | $R^9$ | $R^{10}$ | Geranyl 2,3-double Bond configuration | Compound |
|---|---|---|---|---|---|
| 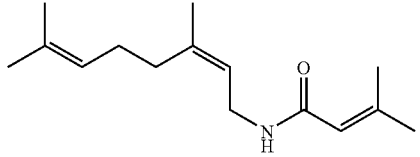 | | Me | Me | Z | |

These compounds and uses thereof have been found beneficial in augmenting or imparting an olfactory effect taste enhancement or somatosensory effect to a foodstuff, chewing gum, medicinal product, toothpaste, alcoholic beverage, aqueous beverage, snack, sauce or soup particularly providing a (a) umami taste, (b) salt effects, (c) flavor enhancement, and (d) preferred overall flavor profile.

More specifically, examples of the organoleptic properties for the dienalkylamides of our invention are as follows:

| $R^7$ | $R^8$ | $R^9$ | $R^{10}$ | Compound | Taste profile |
|---|---|---|---|---|---|
| Cyclopropyl | | Me | Me | | Salt, MSG, Umami, mouthfeel, lasting sweetness. |
| Cyclopropyl | | Me | Me | | Salty, MSG, Umami, brothy, mouthfeel, sweetness. |
| Me | Me | Me | Me | | Some salt enhancement, umami and strong MSG effect |
| Me | Me | Me | Me | | Salt enhancement, MSG enhancement, Umami, brothy. |

Other novel compounds of the present invention include the following according to Structure 1 above:

| R1 | R2 | R3 | R4 | R5 | R6 | Compound Double bond configuration as per drawing |
|---|---|---|---|---|---|---|
| H | cyclopropyl | H | H | | $CH_3(CH_2)_4CH=CHCH_2CH_2$ | 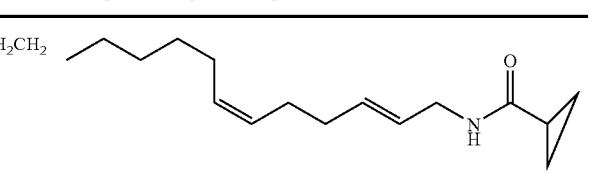 |

-continued
| R1 | R2 | R3 | R4 | R5 | R6 | | Compound Double bond configuration as per drawing |
|---|---|---|---|---|---|---|---|
| H | cyclopropyl | H | Me | | 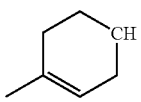 | | 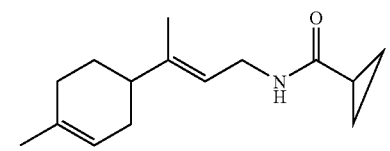 |
| H | cyclopropyl | H | Me | | 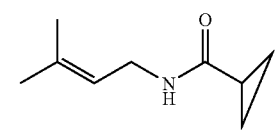 | | 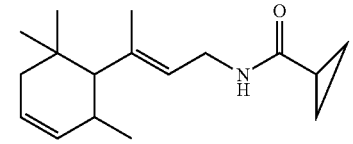 |
| H | cyclopropyl | H | Me | Me | | | 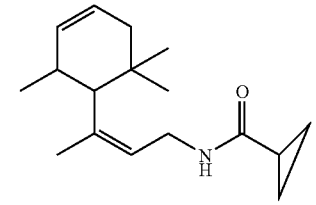 |
| H | cyclopropyl | H | Me | | 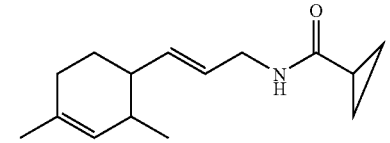 | | 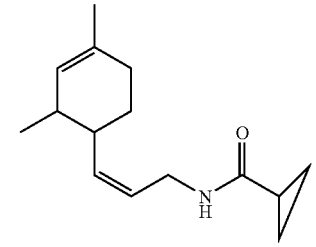 |
| H | cyclopropyl | H | Me | | 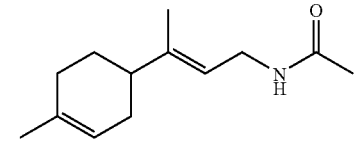 | | |
| H | cyclopropyl | H | H | | | | |
| H | cyclopropyl | H | H | | | | |
| H | H | H | H | Me | | | |

| R1 | R2 | R3 | R4 | R5 | R6 | Compound Double bond configuration as per drawing | |
|---|---|---|---|---|---|---|---|
| H | H | H | H | Me | 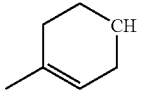 | 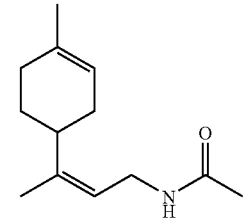 | |
| H | H | H | H | Me | 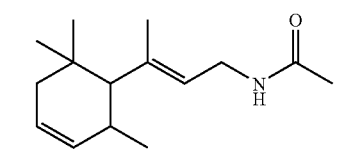 | 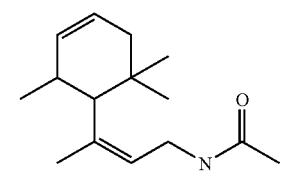 | |
| H | H | H | H | Me | 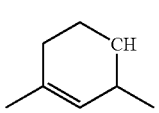 | 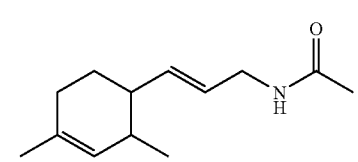 | |
| H | H | H | H | H | 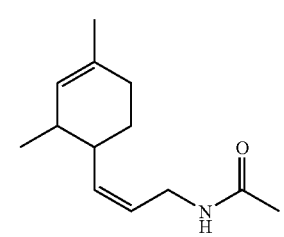 | 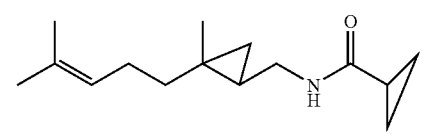 | |
| H | H | H | H | H | 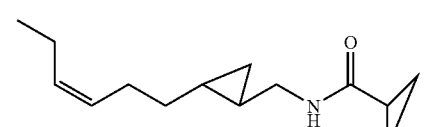 | | |
Other compounds of the present invention include the following according to Structure 2 above:
| R1 | R2 | R3 | R4 | R5 | R6 | Compound |
|---|---|---|---|---|---|---|
| H | cyclopropyl | H | Me | (CH₃)₂C=CHCH₂CH₂ | | |
| H | cyclopropyl | H | H | CH₃CH₂CH=CHCH₂CH₂ | | |

The following compounds and Chemical Abstract (CA) names are provided for various compounds of the present invention.

| Compound # | Structure (Novel compounds) | CA Index Name |
|---|---|---|
| 1 | | 2,6-nonadienamide, N-[(2E)-3,7-dimethyl-2,6-octadienyl]-, (2E,6Z)- |
| 2 | | 2,6-nonadienamide, N-[(2Z)-3,7-dimethyl-2,6-octadienyl]-, (2E,6Z)- |
| 3 | | 2,6-octadienamide, N-[(2E)-3,7-dimethyl-2,6-octadienyl]-3,7-dimethyl-, (2E)- |
| 4 | | 2,6-octadienamide, N-[(2Z)-3,7-dimethyl-2,6-octadienyl]-3,7-dimethyl-, (2E)- |
| 5 | | 2,6-octadienamide, N-[(2E)-3,7-dimethyl-2,6-octadienyl]-3,7-dimethyl-, (2Z)- |
| 6 | | 2,6-octadienamide, N-[(2Z)-3,7-dimethyl-2,6-octadienyl]-3,7-dimethyl-, (2Z)- |
| 7 | | 2,6-octadienamide, 3,7-dimethyl-N-[(2Z,6Z)-2,6-nonadienyl]-, (2E)- |
| 8 | | 2,6-octadienamide, 3,7-dimethyl-N-[(2Z,6Z)-2,6-nonadienyl]-, (2Z)- |
| 9 | | cyclopropanecarboxamide, N-[(2Z,6Z)-2,6-nonadienyl]- |

| Compound # | Structure (Novel compounds) | CA Index Name |
|---|---|---|
| 10 | | cyclopropanecarboxamide, N-[(2E,6Z)-2,6-nonadienyl]- |
| 11 | | cyclopropanecarboxamide, N-[(2E)-3-(3-cyclohexen-1-yl)-2-propenyl]- |
| 12 | | cyclopropanecarboxamide, N-[(2Z)-3-(3-cyclohexen-1-yl)-2-propenyl]- |
| 13 | | cyclopropanecarboxamide, N-[(2E)-2-methyl-3-phenyl-2-propenyl]- |
| 14 | | cyclopropanecarboxamide, N-[(2Z)-2-methyl-3-phenyl-2-propenyl]- |
| 15 | | cyclopropanecarboxamide, N-[(2E)-3-phenyl-2-butenyl]- |
| 16 | | cyclopropanecarboxamide, N-[(2Z)-3-phenyl-2-butenyl]- |
| 17 | | cyclopropanecarboxamide, N-[(2Z,6Z)-2-methyl-2,6-nonadienyl]- |
| 18 | | cyclopropanecarboxamide, N-[(2E,6Z)-2-methyl-2,6-nonadienyl]- |

-continued

| Compound # | Structure (Novel compounds) | CA Index Name |
|---|---|---|
| 19 | 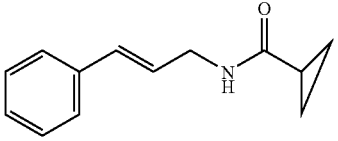 | cyclopropanecarboxamide, N-[(2E)-3-phenyl-2-propenyl]- |
| 20 | 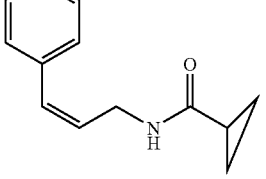 | cyclopropanecarboxamide, N-[(2Z)-3-phenyl-2-propenyl]- |
| 21 | 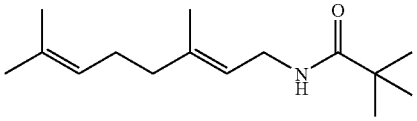 | propanamide, N-[(2E)-3,7-dimethyl-2,6-octadienyl]-2,2-dimethyl- |
| 22 | 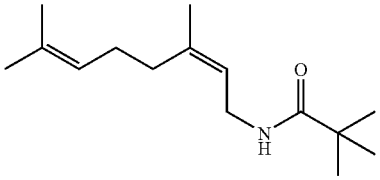 | propanamide, N-[(2Z)-3,7-dimethyl-2,6-octadienyl]-2,2-dimethyl- |
| 23 | 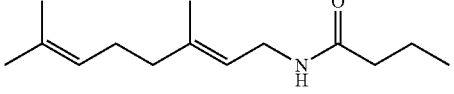 | butanamide, N-[(2E)-3,7-dimethyl-2,6-octadienyl]- |
| 24 | 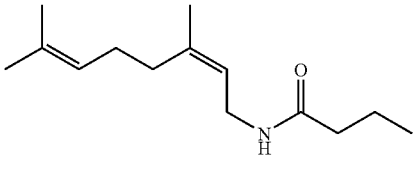 | butanamide, N-[(2Z)-3,7-dimethyl-2,6-octadienyl]- |
| 25 | 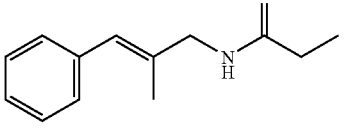 | propanamide, N-[(2E)-2-methyl-3-phenyl-2-propenyl]- |
| 26 | 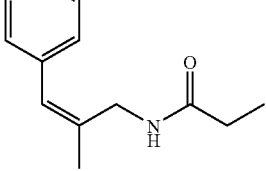 | propanamide, N-[(2Z)-2-methyl-3-phenyl-2-propenyl]- |
| 27 | 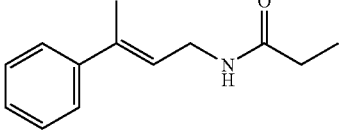 | propanamide, N-[(2E)-3-phenyl-2-butenyl]- |

-continued

| Compound # | Structure (Novel compounds) | CA Index Name |
|---|---|---|
| 28 | | propanamide, N-[(2Z)-3-phenyl-2-butenyl]- |
| 29 | | acetamide, N-[(2E)-2-methyl-3-phenyl-2-propenyl]- |
| 30 | | acetamide, N-[(2Z)-2-methyl-3-phenyl-2-propenyl]- |
| 31 | | acetamide, N-[(2E)-3-phenyl-2-butenyl]- |
| 32 | | acetamide, N-[(2Z)-3-phenyl-2-butenyl]- |
| 33 | | acetamide, N-[(2Z,6Z)-2-methyl-2,6-nonadienyl]- |
| 34 | | acetamide, N-[(2E,6Z)-2-methyl-2,6-nonadienyl]- |
| 35 | | propanamide, N-[(2E)-3-(3-cyclohexen-1-yl)-2-propenyl]- |
| 36 | | propanamide, N-[(2Z)-3-(3-cyclohexen-1-yl)-2-propenyl]- |

-continued

| Compound # | Structure (Novel compounds) | CA Index Name |
|---|---|---|
| 37 | | acetamide, N-[(2E)-3-(3-cyclohexen-1-yl)-2-propenyl]- |
| 38 | | acetamide, N-[(2Z)-3-(3-cyclohexen-1-yl)-2-propenyl]- |
| 39 | | propanamide, N-[(2E)-3-(3-cyclohexen-1-yl)-2-propenyl]-2,2-dimethyl- |
| 40 | | propanamide, N-[(2Z)-3-(3-cyclohexen-1-yl)-2-propenyl]-2,2-dimethyl- |
| 41 | | butanamide, N-[(2E)-3,7-dimethyl-2,6-octadienyl]-2-methyl- |
| 42 | | butanamide, N-[(2Z)-3,7-dimethyl-2,6-octadienyl]-2-methyl- |
| 43 | | cyclopropanecarboxamide, N-[(2E)-3,7-dimethyl-2,6-octadienyl]- |
| 44 | | cyclopropanecarboxamide, N-[(2Z)-3,7-dimethyl-2,6-octadienyl]- |
| 45 | | propanamide, N-[(2E)-3,7-dimethyl-2,6-octadienyl]-2-methyl- |

| Compound # | Structure (Novel compounds) | CA Index Name |
|---|---|---|
| 46 | | propanamide, N-[(2Z)-3,7-dimethyl-2,6-octadienyl]-2-methyl- |
| 47 | | 2-butenamide, N-[(2E)-3,7-dimethyl-2,6-octadienyl]-, (2E)- |
| 48 | | 2-butenamide, N-[(2Z)-3,7-dimethyl-2,6-octadienyl]-, (2E)- |
| 49 | | 2-butenamide, N-[(2E)-3,7-dimethyl-2,6-octadienyl]-3-methyl- |
| 50 | | 2-butenamide, N-[(2Z)-3,7-dimethyl-2,6-octadienyl]-3-methyl- |
| 51 | | cyclopropanecarboxamide, N-[(2E,6Z)-2,6-dodecadienyl]- |
| 52 | | cyclopropanecarboxamide, N-[(2E)-3-(4-methyl-3-cyclohexen-1-yl)-2-butenyl]- |
| 53 | | cyclopropanecarboxamide, N-[(2Z)-3-(4-methyl-3-cyclohexen-1-yl)-2-butenyl]- |
| 54 | | cyclopropanecarboxamide, N-(3-methyl-2-butenyl)- |

-continued

| Compound # | Structure (Novel compounds) | CA Index Name |
|---|---|---|
| 55 | | cyclopropanecarboxamide, N-[(2E)-3-(2,6,6-trimethyl-3-cyclohexen-1-yl)-2-butenyl]- |
| 56 | | cyclopropanecarboxamide, N-[(2Z)-3-(2,6,6-trimethyl-3-cyclohexen-1-yl)-2-butenyl]- |
| 57 | | cyclopropanecarboxamide, N-[(2E)-3-(2,4-dimethyl-3-cyclohexen-1-yl)-2-propenyl]- |
| 58 | | cyclopropanecarboxamide, N-[(2Z)-3-(2,4-dimethyl-3-cyclohexen-1-yl)-2-propenyl]- |
| 59 | | acetamide, N-[(2E)-3-(4-methyl-3-cyclohexen-1-yl)-2-butenyl]- |
| 60 | | acetamide, N-[(2Z)-3-(4-methyl-3-cyclohexen-1-yl)-2-butenyl]- |
| 61 | | acetamide, N-[(2E)-3-(2,6,6-trimethyl-3-cyclohexen-1-yl)-2-butenyl]- |
| 62 | | acetamide, N-[(2Z)-3-(2,6,6-trimethyl-3-cyclohexen-1-yl)-2-butenyl]- |

-continued

| Compound # | Structure (Novel compounds) | CA Index Name |
|---|---|---|
| 63 | | acetamide, N-[(2E)-3-(2,4-dimethyl-3-cyclohexen-1-yl)-2-propenyl]- |
| 64 | | acetamide, N-[(2Z)-3-(2,4-dimethyl-3-cyclohexen-1-yl)-2-propenyl]- |
| 65 | | cyclopropanecarboxamide, N-[[2-methyl-2-(4-methyl-3-pentenyl)cyclopropyl]methyl]- |
| 66 | | cyclopropanecarboxamide, N-[[2-[(3Z)-3-hexenyl]cyclopropyl]methyl]- |
| 67 | | propanamide, N-[(2E)-3,7-dimethyl-2,6-octadienyl]- |
| 68 | | propanamide, N-[(2Z)-3,7-dimethyl-2,6-octadienyl]- |
| 69 | | acetamide, N-[(2E)-3,7-dimethyl-2,6-octadienyl]- |
| 70 | | acetamide, N-[(2Z)-3,7-dimethyl-2,6-octadienyl]- |

We have surprisingly found the literature has not previously reported dienalkylamides, alkenylamides, or cyclopropylic amides as having or enhancing umami flavor. In addition, closely structurally related compounds such as dienals and unsaturated acids, are not specifically reported to possess umami character when tasted in isolation. In addition the ability to provide an enhanced saltiness for the product without increasing sodium level is not disclosed or suggested by the prior art. The salt enhancing properties of the compounds of the present invention are important because it allows flavorists to provide the desired salty taste profile in foods and beverages without actually having higher salt levels in the food. Therefore the consumer can have both the taste profile that they desire while without having the adverse health effects associated with increased salt levels such as hypertension.

As used herein olfactory effective amount is understood to mean the amount of compound in flavor compositions the individual component will contribute to its particular olfactory characteristics, but the flavor, taste and aroma effect on the overall composition will be the sum of the effects of each of the flavor ingredients. As used herein taste effects include salt, sweet and umami effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of cyclopropylic amides, alkenylamides and dienalkylamides used in products is greater than 50 parts per billion, generally provided at a level of from about 0.01 parts per million to about 50 parts per million in the finished product, more preferably from about 0.1 parts per million to about 20 parts per million by weight, and in preferred embodiments from about 0.5 to about 5 parts per million.

The usage level of cyclopropylic amides, alkenylamides, and dienalkylamides varies depending on the product in which the dienalkylamides are employed. For example, alcoholic beverages the usage level is from about 0.1 to about 5 parts per million, preferably from about 0.5 to about 3 and most preferably from about 1 to about 2 parts per million by weight. Non-alcoholic beverages are flavored at levels of from about 0.05 parts per million to about 5 parts per million, preferably from about 0.1 parts per billion to about 2 parts per million and in highly preferred situations of from about 0.7 to about 1 parts per billion. Other products such as snack foods, candy and gum products can be advantageously flavored using compounds of the present invention at levels described above.

Among the preferred compounds of the present invention are:

2-butenamide, N-[(2E)-3,7-dimethyl-2,6-octadienyl]-, (2E)-2-butenamide, N-[(2Z)-3,7-dimethyl-2,6-octadienyl]-, (2E)-2-butenamide, N-[(2E)-3,7-dimethyl-2,6-octadienyl]-3-methyl-2-butenamide, N-[(2Z)-3,7-dimethyl-2,6-octadienyl]-3-methyl-cyclopropanecarboxamide, N-[(2Z,6Z)-2,6-nonadienyl]-cyclopropanecarboxamide, N-[(2E,6Z)-2,6-nonadienyl]-cyclopropanecarboxamide, N-[(2E)-3-(3-cyclohexen-1-yl)-2-propenyl]-cyclopropanecarboxamide, N-[(2E,6Z)-2,6-dodecadienyl]-cyclopropanecarboxamide, N-[(2E)-3,7-dimethyl-2,6-octadienyl]-cyclopropanecarboxamide, N-[(2Z)-3,7-dimethyl-2,6-octadienyl]-

The present invention also provides a method for enhancing or modifying the salt flavor of a food through the incorporation of an organoleptically acceptable level of the compounds described herein. The compounds can be used individually or in combination with other salt enhancing compounds of the present invention. In addition, the salt enhancing materials of the present invention can be used in combination with other salt enhancing compositions known in the art, including those materials listed in co-pending applications U.S. Ser. No. 10/919,631 filed on Aug. 17, 2004; U.S. Ser. No. 10/861,751 filed on Jun. 4, 2004; and U.S. Ser. No. 10/783,652 filed Feb. 20, 2004; and also include cetylpyridium chloride, bretylium tosylate, various polypeptides, mixtures of calcium salts of ascorbic acid, sodium chloride and potassium chloride, as described in various U.S. Pat. Nos. 4,997,672; 5,288,510; 6,541,050 and U.S. Patent Application 2003/0091721.

The salt taste enhancing compounds of the present invention may be employed to enhance the perceived salt taste of any salts used in food or beverage products. The preferred salt taste to be enhanced by the compounds of the present invention is that of sodium chloride, primarily because of the discovery that ingestion of large amounts of sodium may have adverse effects on humans and the resultant desirability of reducing salt content while retaining salt taste.

In addition, the compounds of the present invention may also be employed to enhance the perceived salt taste of known salty tasting compounds which may be used as salt substitutes, including potassium chloride and ribonucleotides. Suitable compounds also include cationic amino acids and low molecular weight dipeptides. Specific examples of these compounds are arginine hydrochloride, arginine ammonium chloride, lysine hydrochloride and lysine-ornithine hydrochloride. These compounds exhibit a salty taste but are typically useful only at low concentrations since they exhibit a bitter flavor at higher concentrations. Thus, it is feasible to reduce the sodium chloride content of a food or beverage product by first formulating a food or beverage with less sodium chloride than is necessary to achieve a desired salt taste and then adding to said food or beverage the compounds of the present invention in an amount sufficient to potentiate the salt taste of said salted food or beverage to reach said desired taste. In addition, the sodium chloride content may be further reduced by substituting a salty-tasting cationic amino acid, a low molecular weight dipeptide or mixtures thereof for at least a portion of the salt.

In a preferred embodiment of the present invention we have found the compound of the present invention are materials used in combination with each other or other salt enhancing materials in weight ratios of from about 1:10 to about 10:1, typically from about 1:3 to about 3:1; more preferably from about 1:1 on a weight basis.

In a highly preferred embodiment we have discovered that the compounds of the present invention when used in combination with the compounds disclosed in co-pending application U.S. Ser. No. 10/783,652 filed Feb. 20, 2004. The preferred compounds disclosed in this application include but are not limited to:

N,N,3,7-Tetramethylocta-2,6-dienamide, (2E)-2-propenamide, 3-(3-cyclohexen-1-yl)-N-ethyl-, (2E)-3,7-dimethyl-2,6-octadienamide, N-ethyl-, (2E)-2,6-nonadienamide, N,N-dimethyl-, (2E,6Z)-2,6-nonadienamide, N-cyclopropyl, 2-methyl-, (2E,6Z)-2,6-dodecadienamide, N-ethyl-, (2E,6Z)-2,6-nonadienamide, N-cyclopropyl-, (2E,6Z)-2,6-nonadienamide, N-ethyl-, (2E,6Z)-

The mixtures of the compounds range from about 1:10 to 10:1 weight percent, preferably from about 1:5 to about 5:1 weight percent, most preferably in a 1:2 to a 2:1 weight ratio of the compounds.

Combinations that have been found to provide high levels of salt enhancing effects to products are compounds of the present invention:

2-butenamide, N-[(2E)-3,7-dimethyl-2,6-octadienyl]-, (2E)-2-butenamide, N-[(2Z)-3,7-dimethyl-2,6-octadienyl]-, (2E)-2-butenamide, N-[(2E)-3,7-dimethyl-2,6-octadienyl]-3-methyl-2-butenamide, N-[(2Z)-3,7-dimethyl-2,6-octadienyl]-3-methyl-cyclopropanecarboxamide, N-[(2Z,6Z)-2,6-nonadienyl]-cyclopropanecarboxamide, N-[(2E,6Z)-2,6-nonadienyl]-cyclopropanecarboxamide, N-[(2E)-3-(3-cyclohexen-1-yl)-2-propenyl]-cyclopropanecarboxamide, N-[(2E,6Z)-2,6-dodecadienyl]-cyclopropanecarboxamide, N-[(2E)-3,7-dimethyl-2,6-octadienyl]-cyclopropanecarboxamide, N-[(2Z)-3,7-dimethyl-2,6-octadienyl]-N,N,3,7-Tetramethylocta-2,6-dienamide, (2E)-2-propenamide, 3-(3-cyclohexen-1-yl)-N-ethyl-, (2E)-3,7-dimethyl-2,6-octadienamide, N-ethyl-, (2E)-2,6-nonadienamide, N,N-dimethyl-, (2E,6Z)-2,6-nonadienamide, N-cyclopropyl, 2-methyl-, (2E,6Z)-2,6-dodecadienamide, N-ethyl-, (2E,6Z)-2,6-nonadienamide, N-cyclopropyl-, (2E,6Z)-2,6-nonadienamide, N-ethyl-, (2E,6Z)-.

The highly preferred weight ratios of these mixtures is from about 2:1 to about 1:2 on a weight basis. Most highly preferred combination is the mixture of cyclopropanecarboxamide, N-[(2E)-3,7-dimethyl-2,6-octadienyl]- with 2,6-nonadienamide, N-cyclopropyl-, (2E,6Z)- and 2,6-nonadienamide, N-ethyl-, (2E,6Z)- in the ratio about 2:1:1 by weight, with a total use level of 8 ppm. For purpose of illustration that would be a usage level of about 4, 2 and 2 parts per million respectively by weight in a product such as a foodstuff.

The term "foodstuff" as used herein includes both solid and liquid ingestible materials for man or animals, which materials usually do, but need not, have nutritional value. Thus, foodstuffs include food products, such as, meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the compounds of our invention; (2) that they be organoleptically compatible with the compounds of our invention whereby the flavor of the ultimate consumable material to which the compounds are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the dienalkylamides of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimethoxy-phenol; amyl acetate; amyl cinnamate; γ-butyryl lactone; furfural; trimethylpyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methylpyrazine; tetramethylpyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; mono-potassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethylpyrazine; propylpropenyl disulfide; propylpropenyl trisulfide; diallyl disulfide; diallyl trisulfide; dipropenyl disulfide; dipropenyl trisulfide; 4-methyl-2-[(methyl-thio)-ethyl]-1,3-dithiolane; 4,5-dimethyl-2-(methylthiomethyl)-1,3-dithiolne; and 4-methyl-2-(methylthiomethyl)-1,3-dithiolane. These and other flavor ingredients are provided in U.S. Pat. Nos. 6,110,520 and 6,333,180.

The cyclopropylic amides, alkenylamides, and dienalkylamides of our invention or compositions incorporating them, as mentioned above, can be combined with one or more vehicles or carriers for adding them to the particular product. Vehicles can be edible or otherwise suitable materials such as ethyl alcohol, propylene glycol, water and the like, as described above. Carriers include materials such as gum arabic, carrageenan, xanthan gum, guar gum and the like.

Cyclopropylic amides, alkenylamides, and dienalkylamides prepared according to our invention can be incorporated with the carriers by conventional means such as spray-drying, extrusion, drum-drying and the like. Such carriers can also include materials for coacervating the dienalkylamides of our invention to provide encapsulated products, as set forth above. When the carrier is an emulsion, the flavoring composition can also contain emulsifiers such as mono- and diglycerides or fatty acids and the like. With these carriers or vehicles, the desired physical form of the compositions can be prepared.

The quantity of cyclopropylic amides, alkenylamides, and dienalkylamides utilized should be sufficient to impart the desired flavor characteristic to the product, but on the other hand, the use of an excessive amount of the compounds is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology "organoleptically effective amount" and "sufficient amount" is understood in the context of the present invention to be quantitatively adequate to alter the flavor of the foodstuff.

With reference to the novel compounds of our invention, the synthesis is effected by means of the reaction of acid anhydride with amine, added either directly or in solution, according to the general scheme:

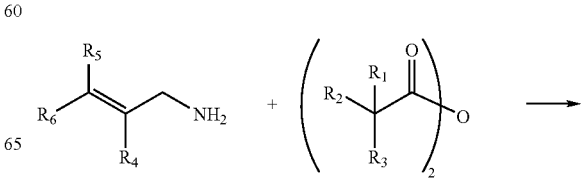

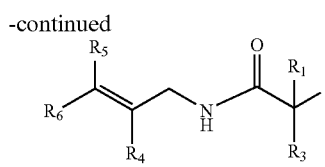

where $R^1$, $R^2$, $R^3$, $R^4$, $R^5$ and $R^6$ have the meaning set forth in formula I, and structures 1 and 2 set forth above.

The synthesis of amine follows a literature procedure [The Journal of Organic Chemistry 1989, 54, 3292-3303]. The acid anhydride is dissolved in hexanes to which amine is added in 0.9 to 1.0 equivalent at temperatures ranging 0° C. to room temperature, most preferably from 10° C. to 20° C. The resulting solution is aged for about 1-3 hours at room temperature.

The reaction can be quenched with aqueous sodium chloride, hydrogen chloride or sodium hydroxide depending upon the need to remove residual acid or amine. The mixture is extracted into ethereal solvent, washed to neutrality and solvent removed.

The crude product is purified by distillation or recrystallization depending on the physical properties. The reaction occurs in 35-70% mole yield based on amine.

In the case when acid anhydride is not readily available, the synthesis is effected by means of the reaction of acid with ethyl chloroformate in the presence of triethylamine and further reaction of the intermediate with amine, added either directly or in solution, according to the general scheme:

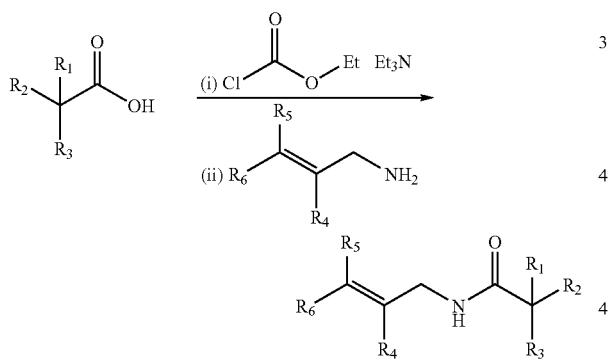

where $R^1$, $R^2$, $R^3$, $R^4$, $R^5$ and $R^6$ have the meaning set forth in formula I, and structures 1 and 2 set forth above.

The acid is dissolved in dichloromethane to which ethyl chloroformate is added in 1.0 to 2.0 equivalents at temperatures ranging from 0° C. to room temperature, most preferably from 10° C. to 20° C. The resulting solution is cooled to −10° C. to −30° C., and triethylamine is added in 1.0 to 2.0 equivalents such that the temperature range is below 0° C. and the mixture aged for 1 hour.

The mixture is filtered, and the filtrate cooled to 0° C. The amine is added in 1.0 to 7.0 equivalents either neat or as a solution in a suitable solvent, the reaction is then aged for about 1-3 hours at room temperature.

The reaction can be quenched with aqueous sodium chloride, hydrogen chloride or sodium hydroxide depending upon the need to remove residual acid or amine. The mixture is extracted into ethereal solvent or dichloromethane, washed to neutrality and solvent removed.

The crude product is purified by distillation or re-crystallization depending on the physical properties.

The reaction occurs in 35-75% mole yield based on acid.

The dienalkylamides of the present invention can be admixed with other flavoring agents and incorporated into foodstuffs and other products using techniques well known to those with ordinary skill in the art. Most commonly the dienalkylamides are simply admixed using the desired ingredients within the proportions stated.

The following are provided as specific embodiments of the present invention. Other modifications of this invention will be readily apparent to those skilled in the art, without departing from the scope of this invention. As used herein, in both the specification and following examples, all percentages are understood to be weight percent unless noted to the contrary.

All U.S. patents and U.S. patent applications cited herein are incorporated by reference as if set forth in their entirety. Upon review of the foregoing, numerous adaptations, modifications, and alterations will occur to the reviewer. These will all be, however, within the spirit of the present invention. Accordingly, reference should be made to the appended claims in order to ascertain the true scope of the present invention.

EXAMPLE 1

Preparation of Materials of the Present Invention

The following reaction sequence was used to prepare the specific compounds described by the NMR data set forth below:

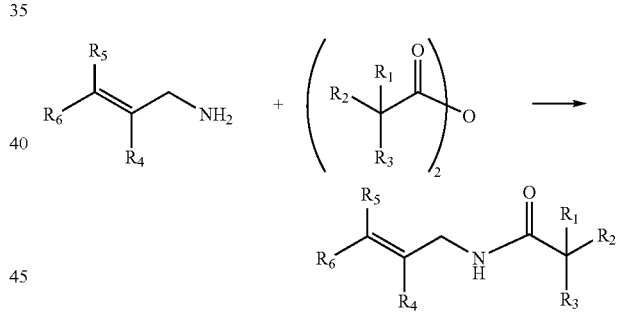

where $R^1$, $R^2$, $R^3$, $R^4$, $R^5$ and $R^6$ have the meaning set forth in formula I, and structures 1 and 2 set forth above.

The acid anhydride was dissolved in hexanes to which amine was added in 0.9 to 1.0 equivalent at temperatures ranging from 0° C. to room temperature, most preferably from 10° C. to 20° C. The resulting solution was aged for about 1-3 hours at room temperature.

The reaction was quenched with aqueous sodium chloride, hydrogen chloride or sodium hydroxide depending upon the need to remove residual acid or amine. The mixture was extracted into ethereal solvent, washed to neutrality and solvent removed.

The crude product was purified by distillation or recrystallization depending on the physical properties.

The amides were synthesized according to the general scheme above with the following specific examples. Equivalents set out are mole equivalents based on starting amine, yields were distilled chemical yields based on starting amine.

Butanamide, N-[(2E)-3,7-dimethyl-2,6-octadienyl]-

Butyric anhydride 1.1 eq, 3,7-dimethylocta-2E,6-dienylamine 1 eq, quenched with 10% sodium hydroxide, yield=35%.

0.95 ppm (3H, t, J=7.34 Hz), 1.60 ppm (3H, s), 1.62-1.71 ppm (2H, m), 1.67 ppm (3H, s), 1.68 ppm (3H, s), 2.01 ppm (2H, m), 2.08 ppm (2H, m), 2.15 ppm (2H, m), 3.85 ppm (2H, m), 5.08 ppm (1H, m), 5.19 ppm (1H, m), 5.44 ppm (1H, br. s).

2-butenamide, N-[(2E)-3,7-dimethyl-2,6-octadienyl]-, (2E)

Crotonic anhydride 1.1 eq, 3,7-dimethylocta-2E,6-dienylamine 1 eq, quenched with 10% sodium hydroxide, yield=70%.

1.60 ppm (3H, s), 1.68 ppm (6H, m), 1.84-1.91 ppm (3H, m), 1.94-2.09 ppm (4H, m), 3.84 ppm (1H, m), 3.91 ppm (1H, m), 5.08 ppm (1H, m), 5.21 ppm (1H, m), 5.34 ppm (1H, br. s), 5.79 ppm (1H, d, J=15.15 Hz), 6.84 ppm (1H, m).

Propanamide, N-[(2E)-3,7-dimethyl-2,6-octadienyl]-2-methyl-

2-Methylpropionic anhydride 1.1 eq, 3,7-dimethylocta-2E,6-dienylamine 1 eq, quenched with 10% sodium hydroxide, yield=58%.

1.17 ppm (d, 6H, J=6.5 Hz), 1.63 ppm (3H, s), 1.69 ppm (3H, s), 1.71 ppm (3H, s), 2.04 ppm (2H, m), 2.08 ppm (2H, m), 2.82 (1H, m), 3.87 ppm (2H, m), 5.10 ppm (1H, m), 5.26 ppm (1H, m), 5.56 ppm (1H, br. s).

EXAMPLE 2

Preparation of Materials of the Present Invention

The following reaction sequence was used to prepare the specific compounds described by the NMR data set forth below:

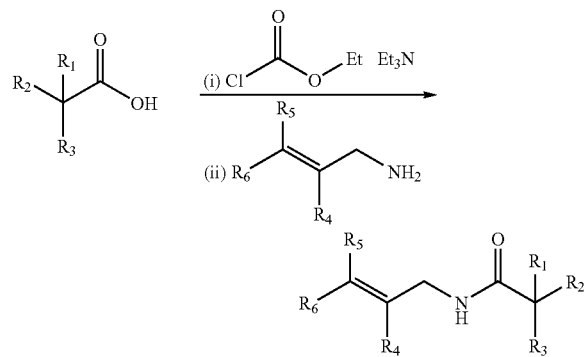

The acid was dissolved in dichloromethane to which ethyl chloroformate was added in 1.0 to 2.0 equivalents at temperatures ranging from 0° C. to room temperature, most preferably from 10° C. to 20° C. The resulting solution was cooled to −10° C. to −30° C., and triethylamine is added in 1.0 to 2.0 equivalents such that the temperature range was below 0° C. and the mixture aged for 1 hour.

The mixture was filtered, and the filtrate cooled to 0° C. The amine was added in 1.0 to 7.0 equivalents either neat or as a solution in THF and the reaction was aged for about 1-3 hours at room temperature.

The reaction was quenched with aqueous sodium chloride, hydrogen chloride or sodium hydroxide depending upon the need to remove residual acid or amine. The mixture was extracted into ethereal solvent or dichloromethane, washed to neutrality and solvent removed.

The crude product was purified by distillation or recrystallization depending on the physical properties.

The amides were synthesized according to the general scheme above with the following specific examples. Equivalents set out are mole equivalents based on starting acid, yields were distilled chemical yields based on starting acid.

Cyclopropanecarboxamide, N-[(2E)-3,7-dimethyl-2,6-octadienyl]-

Cyclopropanecarboxylic acid 1 eq, ethyl chloroformate 1.5 eq, triethylamine 1.5 eq, 3,7-dimethylocta-2E,6-dienylamine 1.6 eq, quench with 10% sodium chloride solution, yield=36%.

0.71 ppm (2H, m), 0.96 ppm (2H, m), 1.33 ppm (1H, m), 1.60 ppm (3H, s), 1.67 ppm (3H, s), 1.69 ppm (3H, s), 2.01 ppm (2H, m), 2.08 ppm (2H, m), 3.87 ppm (2H, m), 5.08 ppm (1H, m), 5.21 ppm (1H, m), 5.61 ppm (1H, br. s).

EXAMPLE 3

Taste tests were conducted with various molecules. The following molecule (A) IS disclosed and claimed in this specification. Molecules (B) and (J) are disclosed and claimed as flavor materials in co-pending application U.S. Ser. No. 10/783,652 filed Feb. 20, 2004. These materials were used in the following taste examples.

(A) Cyclopropanecarboxamide,N-[(2E)-3,7-Dimethyl-2,6-Octadienyl]
(B) (2E)-N,N,3,7-Tetramethylocta-2,6-dienamide
(C) 2,6-Nonadienamide,N-2-Propenyl-, (2E,6Z)
(D) N-isobutyl-(E2,Z6)-Nonadienamide
(E) 2,6-Dodecadienamide,N-cyclopropyl-, (2E,6Z)
(F) 2-butenamide, N-ethyl-4-(2,2,3-trimethyl-3-cyclopenten-1-yl)-(2E)
(G) 2,6-Octadienamide N-ethyl-3,7-dimethyl
(H) Glycine N-[(2E,6Z)-1-oxo-2,6-nonadienyl]methyl ester
(I) n-Cyclopropyl-(E2,Z6)-Nonadienamide
(J) 2,6-Nonadienamide, N-ethyl-(2E,6Z)-

A trained consumer panel of about 16 flavorists, evaluated the above molecules in tasting solutions and were asked to rate the perception of salt and umami for each taste solution. The taste solutions presented to the panelists contained 0.3% by weight NaCl, 0.1% MSG and 0.015% Ribotides, a commercially available blend of disodium guanylate and disodium inosinate. The above molecules were added to the tasting solution at 1 and 4 parts per million.

The taste panel found the molecules of the invention increased the salt and umami perception in excess of 40%. This increase in the salty and umami taste of the base was higher than the increase seen when KCl was added to the base at levels of 0.12%, or when the total amount of salt, MSG and ribotides in the base were increased by 40%.

EXAMPLE 4

A trained panel of flavorists and scientists were given a series of paired taste samples containing by weight 0.3% NaCl, 0.1% MSG and 0.015% ribotides. For each member of the panel two samples were prepared. One sample given was the unaltered taste solution, the second sample was the sample one with the addition of one part per million of the above molecules. The panelists found the samples containing the molecules to have higher salt and umami character, the increase in salty and umami perception was increased by up to about 20%.

EXAMPLE 5

An expert panel of flavorists and food technologists were asked to blindly evaluate a series of reduced sodium beef broths containing between one and four ppm of the molecules of this invention set forth above. The panel found the broths to be significantly higher in saltiness and umami mouthfeel.

EXAMPLE 6

A commercially available rice side dish was prepared with and without the addition of compounds from this invention. The above described molecules were added at 3 ppm to the prepared rice mix. The rice mix was then prepared on the stove top according to the directions on the package. An expert panel of flavorists and food technologists were asked to rate the saltiness or the samples. The panel found that the rice samples with the addition of the molecules was significantly saltier than the unflavored reference.

The molecules of this invention were added to a commercially available noodle side dish at 2 ppm. A panel of flavorists and food technologists was presented the flavored and unflavored samples blind and asked to comment on the taste differences. The samples containing the molecules were uniformly rated as saltier than the unflavored samples.

EXAMPLE 7

The panel of flavorists and food technologists used in earlier examples were asked to evaluate a series of reduced sodium chicken broth versus a full sodium chicken broth. In this degree of difference testing, the panel was able to find a significant difference in the taste of chicken broth containing 10% less salt. The panel found the difference in the taste of the low salt sample to be pronounced when the salt was reduced by 15%.

Samples of lower salt chicken broth containing 800 parts per billion of the molecules of the invention provided above were given to this panel for evaluation. The panel could not perceive the difference between the full salt chicken broth and the chicken broth with 15% less salt containing the molecules set forth above. A sample of broth containing molecules of this invention with a 20% reduction in salt was not perceived as significantly different from the full salt broth.

What is claimed is:

1. A compound of structure 1:

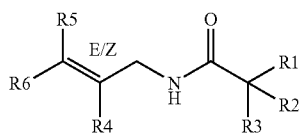

Structure 1 wherein $R^1$=H;
$R^2$ and $R^3$ taken together is selected from the group consisting of cyclopropyl, cyclobutyl, cyclopentyl, cyclopentenyl, cyclohexyl, and cyclohexenyl;
$R^4$ selected from the group consisting of H, methyl and ethyl;
$R^5$ selected from the group consisting of H, methyl and ethyl; and
$R^6$ is selected from the group consisting of alkenyl and alkyldienyl.

2. The compound of claim 1,
wherein $R^1$=H;
$R^2$ and $R^3$ taken together is selected from the group consisting of cyclopropyl, cyclopentyl, cyclopentenyl, cyclohexyl and cyclohexenyl;
$R^4$ selected from the group consisting of H and methyl;
$R^5$ selected from the group consisting of H and methyl; and
$R^6$ is alkenyl.

3. A compound of the formula:

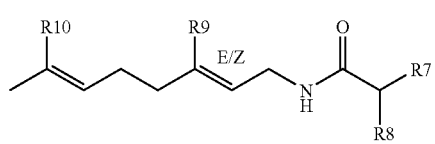

wherein $R^7$ and $R^8$ taken together is cyclopropyl;
$R^9$ selected from the group consisting of H and methyl; and
$R^{10}$ selected from the group consisting of H and methyl.

4. A foodstuff or beverage comprising greater than about 50 parts per billion by weight of the compound of claim 1.

5. A combination of a consumable material selected from the group consisting of a beverage, a foodstuff, a chewing gum, a dental and oral hygiene product and an organoleptically acceptable level of the compound of claim 1.

6. The combination of claim 5, wherein the organoleptically acceptable level of the compound of claim 1 is greater than about 50 parts per billion by weight.

7. The combination of claim 5, wherein the organoleptically acceptable level of the compound of claim 1 is from about 0.01 parts to about 50 parts per million by weight.

8. A method of enhancing the salty taste of a salt-containing consumable material selected from the group consisting of a beverage, a foodstuff, a chewing gum, and a dental and oral hygiene product comprising the step of adding a salt enhancing level of a compound of structure 1:

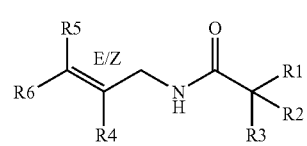

Structure 1 wherein $R^1$=H;
$R^2$ and $R^3$ taken together is selected from the group consisting of cyclopropyl, cyclobutyl, cyclopentyl, cyclopentenyl, cyclohexyl, and cyclohexenyl;
$R^4$ selected from the group consisting of H, methyl and ethyl;
$R^5$ selected from the group consisting of H, methyl and ethyl; and
$R^6$ is selected from the group consisting of alkenyl and alkyldienyl.

9. A combination comprising (a) the compound of claim 1; and (b) an additional salt taste enhancing material, wherein the weight ratio of (a) to (b) is from about 1 to 10 to from about 10 to 1.

10. The combination of claim 9, wherein the weight ratio of (a) to (b) is from about 1 to 5 to from about 5 to 1.

11. The combination of claim 9, wherein the weight ratio of (a) to (b) is from about 1 to 3 to from about 3 to 1.

12. The combination of claim 9, wherein the compound of claim 1 is selected from the group consisting of cyclopropanecarboxamide, N-[(2E)-3,7-dimethyl-2,6-octadienyl]- and cyclopropanecarboxamide, N-[(2Z)-3,7-dimethyl-2,6-octadienyl]-.

13. A foodstuff or beverage containing the combination of claim 9, wherein the the compound of claim 1 is selected from the group consisting of cyclopropanecarboxamide, N-[(2E)-3,7-dimethyl-2,6-octadienyl]- and cyclopropanecarboxamide, N-[(2Z)-3,7-dimethyl-2,6-octadienyl]-.

14. The foodstuff or beverage of claim 13, wherein the additional salt taste enhancing material is selected from the group consisting of
N,N,3,7-Tetramethylocta-2,6-dienamide,(2E)-;
2-propenamide, 3-(3 -cyclohexen-1-yl)-N-ethyl-,(2E)-;
3,7-dimethyl-2,6-octadienamide, N-ethyl-,(2E)-;
2,6-nonadienamide, N,N-dimethyl-, (2E,6Z)-;
2,6-nonadienamide, N-cyclopropyl, 2-methyl-, (2E,6Z)-;
2,6-dodecadienamide, N-ethyl-, (2E,6Z)-;
2,6-nonadienamide, N-cyclopropyl-, (2E,6Z)-; and
2,6-nonadienamide, N-ethyl-, (2E,6Z)-.

15. A process for augmenting, enhancing or imparting an umami taste to a foodstuff, a chewing gum, a medicinal product, a toothpaste, an alcoholic beverage, and an aqueous beverage or soup comprising the step of adding an organoleptically acceptable level of the compound of claim 1.

16. The process of claim 15, wherein the organoleptically acceptable level is greater than about 50 parts per billion by weight.

17. A combination comprising an organoleptically acceptable amount of a compound of structure 1:

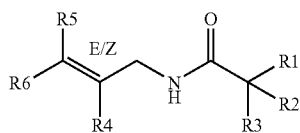

Structure 1 wherein $R^1$=H;
$R^2$ and $R^3$ taken together can represent cyclopropyl, cyclobutyl, cyclopentyl, cyclopentenyl, cyclohexyl, or cyclohexenyl;
$R^4$ selected from the group consisting of H, methyl and ethyl;
$R^5$ selected from the group consisting of H, methyl and ethyl; and
$R^6$ is selected from the group consisting of alkenyl and alkyldienyl; and
sodium chloride.

18. The combination of claim 17 containing an additional salt substitute compound.

19. The combination of claim 18, wherein the additional salt substitute compound is selected from the group consisting of potassium chloride, a ribonucleotide, a cationic amino acid, a low molecular weight dipeptide, a monosodium glutamate and a yeast.

20. The combination of claim 18, wherein the additional salt substitute compound is selected from the group consisting of arginine hydrochloride, arginine ammonium chloride, lysine hydrochloride and lysine-ornithine hydrochloride.

21. A consumable material selected from the group consisting of a foodstuff, a beverage, a chewing gum, a medicinal product, and a toothpaste comprising the combination of claim 17 at a level of greater than about 50 parts per billion by weight.

22. A combination of cyclopropanecarboxamide, N-[(2E)-3,7-dimethyl-2,6-octadienyl]-; 2,6-nonadienamide, N-cyclopropyl-, (2E,6Z)-; and 2,6-nonadienamide, N-ethyl-, (2E, 6Z)-.

23. The combination of claim 22, wherein the weight ratio of cyclopropanecarboxamide, N-[(2E)-3,7-dimethyl-2,6-octadienyl]-; 2,6-nonadienamide, N-cyclopropyl-, (2E,6Z)-; and 2,6-nonadienamide, N-ethyl-, (2E,6Z)- is about 2:1:1.

24. A foodstuff, a beverage, a chewing gum, a medicinal product, or a toothpaste comprising the combination of claim 23.

25. A foodstuff, a beverage, a chewing gum, a medicinal product, or a toothpaste comprising the combination of claim 22 at a level greater than about 50 parts per billion by weight.

* * * * *